United States Patent [19]

Jessel, Jr. et al.

[11] Plant 4,629

[45] Jan. 20, 1981

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 37,574

[22] Filed: May 9, 1979

[51] Int. Cl.[3] ..... A01H 5/00

[52] U.S. Cl. ..... Plt./74

[58] Field of Search ..... Plt./74

*Primary Examiner*—Robert E. Bagwill

*Assistant Examiner*—James R. Feyrer

*Attorney, Agent, or Firm*—Donald D. Jeffery

[57] ABSTRACT

A chrysanthemum plant known by the cultivar name Cherub and particularly characterized as to uniqueness by the combined characteristics of flat capitulum form; anemone capitulum type; lavender ray floret color; diameter across face of capitulum ranging from 45 to 50 mm. at maturity; uniform late nine week flowering response; tall plant height when grown as a pinched spray pot; and semi-spreading branching pattern.

3 Drawing Figures

The present invention comprises a new and distinct cultivar of *Chrysanthemum morifolium, Ramat., hereinafter referred to by the cultivar name Cherub.*

Cherub is a product of a planned breeding program which had the objective of creating new chrysanthemum cultivars with anemone capitulum type, with lavender ray floret color, with eight or nine week flowering response, and with the ability to produce commercially acceptable quality in year round pot mum programs. Such traits in combination were not present in previously available commercial cultivars.

Cherub was originated from a cross made in a controlled breeding program in Barberton, Ohio in 1975. The female parent was #73151009 (unnamed seedling), a dark lavender anemone originated by the present inventors from a cross between #71078020 (unnamed seedling) and #71262006 (unnamed seedling). The male parent of Cherub was #74117006 (unnamed seedling), a lavender pink daisy originated by the present inventors from a cross between #72044014 (unnamed seedling) and #73228002 (unnamed seedling). The seedlings #71078020, #71262006, #72044014, and #73228002 are products of the breeding program of the present inventors.

Cherub was discovered and selected as one flowering plant within the progeny of the stated cross by Walter H. Jessel, Jr. and William E. Duffett on Apr. 27, 1976 in a controlled environment in Barberton, Ohio.

The first act of asexual reproduction of Cherub was accomplished when vegetative cuttings were taken from the initial selection in August, 1976 in a controlled environment in Barberton, Ohio by a technician working under formulations established and supervised by Walter H. Jessel, Jr. and William E. Duffett. Continued asexual reproduction by vegetative cuttings for evaluative tests in flowering and stock programs in conjunction with horticultural examination of selected units initiated June 8, 1977 has demonstrated that the combination of characteristics as herein disclosed for Cherub are firmly fixed and are retained through successive generations of asexual reproduction.

Cherub has not been observed under all possible environmental conditions. The phenotype may vary significantly with variations in environment such as temperature, light intensity, and daylength. The following observations, measurements, and comparisons describe plants grown in Barberton, Ohio and Salinas, Calif. under greenhouse conditions which approximate those generally used in commercial practice.

(1) Flat capitulum form.

(2) Anemone capitulum type.

(3) Lavender ray floret color.

(4) Dark lavender (immature) to lavender (mature) anemome cushion color.

(5) Diameter across face of capitulum ranging from 45 to 50 mm. at maturity.

(6) Uniform late nine week photoperiodic flowering response to short days.

(7) Tall plant height (requiring 1–2 long day weeks prior to pinch and short days, and 2–3 applications 2500 ppm B-9 SP 7 to 21 days after the beginning of short days to attain a flowered plant height of 30 to 45 cm.).

(8) Semi-spreading branching pattern.

The accompanying photographic drawings show typical inflorescence and foliage characteristics of Cherub, with colors being nearly as true as possible with illustrations of this type. Sheet 1 is a color photograph of Cherub as a pot plant. Sheet 2 is a black and white photograph showing three views of the capitulum of Cherub. Sheet 3 is a black and white photograph showing the foliage of Cherub at three stages of growth.

Of the many commercial cultivars known to the present inventors, the most similar in comparison to Cherub are Vedova (unpatented) and Circus (U.S. Plant Pat. No. 4,188). Reference is made to attached Chart A which compares certain characteristics of Cherub to those same characteristics of Vedova and Circus. General comparisons are as follows:

(1) In comparison to Vedova, Cherub has darker lavender ray floret color, more spreading understructure, smaller diameter across face of capitulum, greater responsiveness to B-9 SP for height control, and shorter flowering response period. The capitulum form, capitulum type, and plant height of Cherub are similar to those same characteristics of Vedova.

(2) In comparison to Circus, Cherub has less red (more lavender) ray floret color, different capitulum type, smaller diameter across face of capitulum, and shorter plant height. The branching pattern, capitulum form, responsiveness to B-9 SP for height control, and flowering response period of Cherub are similar to those same characteristics of Circus.

In the following description, color references are made to A Limit Color Cascade, by the Munsell Company, 1972 edition. The color values were determined between 10:00 and 10:30 A.M. on Oct. 13, 1978 under 100 foot-candle light intensity at Salinas, Calif.

Botanical classification: *Chrysanthemum morifolium,* Ramat., cv Cherub.

I. Inflorescence:

A. *Capitulum.*—Form: Flat. Type: Anemone. Diameter across face: 45 to 50 mm.

B. *Corolla of ray florets.*—Color (abaxial): 46-6 to 45-6, oxidizing to 46-4 to 45-4. Color (adaxial): 46-4 to 45-4, oxidizing to 46-2 to 45-2.

C. *Corolla of disc florets.*—Color: Approximately 26-10 over 46-6 (immature), oxidizing from 46-6 to 46-5 (mature).

D. *Reproductive organs.*—Androecium: present disc florets only; scant to numerous; scant pollen. Gynoecium: present both ray and disc florets.

II. Plant:

A. *General appearance.*—Semi-spreading branching pattern; tall height.

B. *Foliage.*—Color (abaxial): approximately 20-15 to 21-15. Color (adaxial): approximately 21-13 overlaid with white.

CHART A

COMPARISON OF CHERUB, VEDOVA and CIRCUS

| CULTIVAR | RAY FLORET COLOR | BRANCHING PATTERN | CAPITULUM TYPE AND FORM |
|---|---|---|---|
| CHERUB | Lavender | Semi-spreading | Flat anemone |
| VEDOVA | Light Lavender | Upright | Flat anemone |

CHART A—Continued

COMPARISON OF CHERUB, VEDOVA and CIRCUS

| CULTIVAR | RAY FLORET COLOR | BRANCHING PATTERN | CAPITULUM TYPE AND FORM |
|---|---|---|---|
| CIRCUS | Lavender Pink | Semi-spreading | Flat daisy |

| CULTIVAR | DIAMETER ACROSS FACE OF CAPITULUM | PLANT HEIGHT | FLOWERING RESPONSE PERIOD |
|---|---|---|---|
| CHERUB | 45 to 50 mm. | Tall; responsive to B-9 SP for height control. | 9 week |
| VEDOVA | 95 to 105 mm. | Tall; not responsive to B-9 SP for height control. | 11 week |
| CIRCUS | 55 to 70 mm. | Medium; responsive to B-9 SP for height control. | 9 week |

COMPARISONS MADE OF PLANTS GROWN AS PINCHED SPRAY POTS IN BARBERTON, OHIO, AND IN SALINAS, CALIFORNIA.

We claim

1. A new and distinct cultivar of *Chrysanthemum morifolium,* Ramat., plant known by the cultivar name of Cherub as described and illustrated and particularly characterized as to uniqueness by the combined characteristics of flat capitulum form, anemone capitulum type, lavender ray floret color, diameter across face of capitulum ranging from 45 to 50 mm. at maturity, uniform late nine week flowering response, tall plant height when grown as a pinched spray pot, and semi-spreading branching pattern.

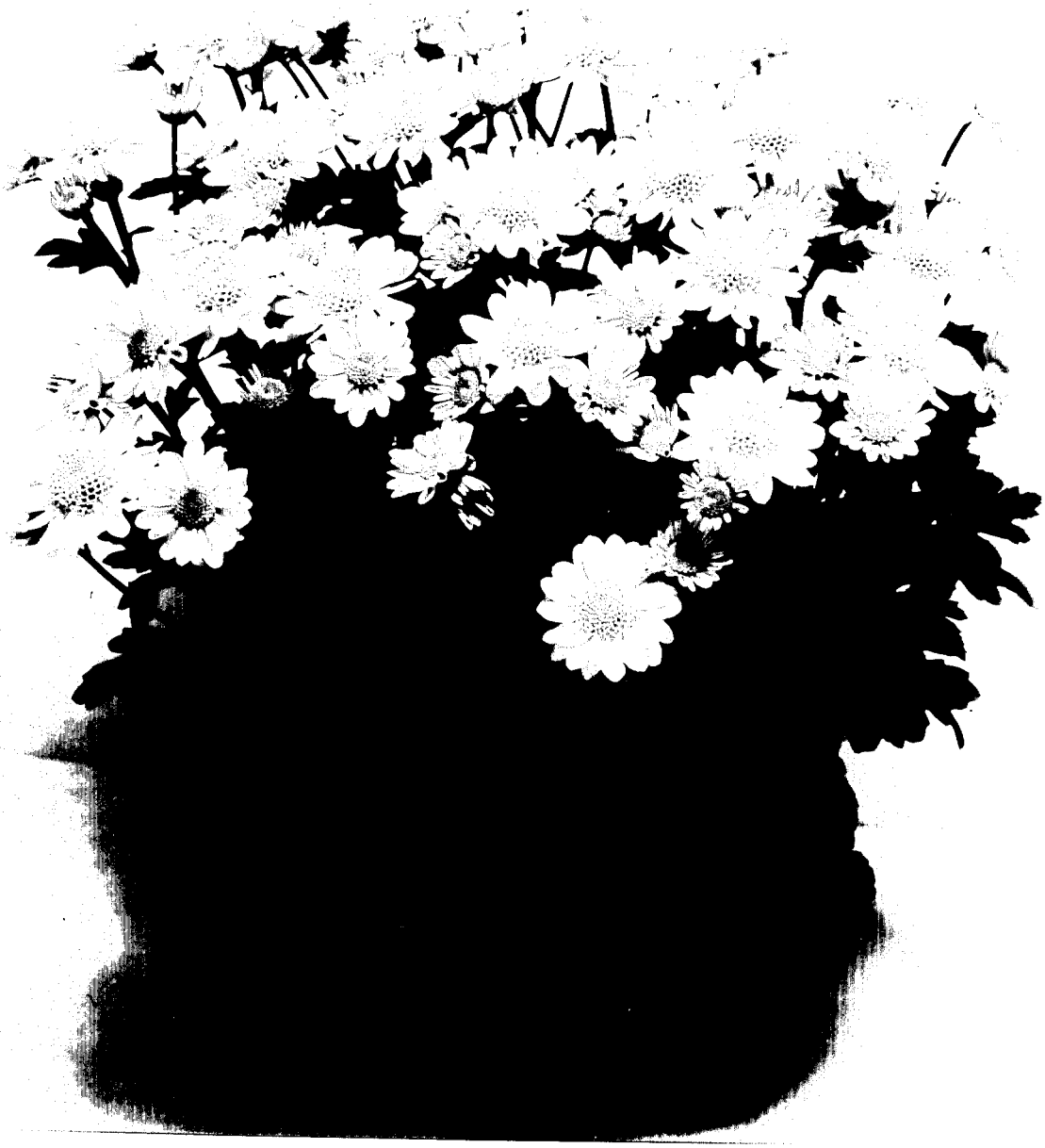

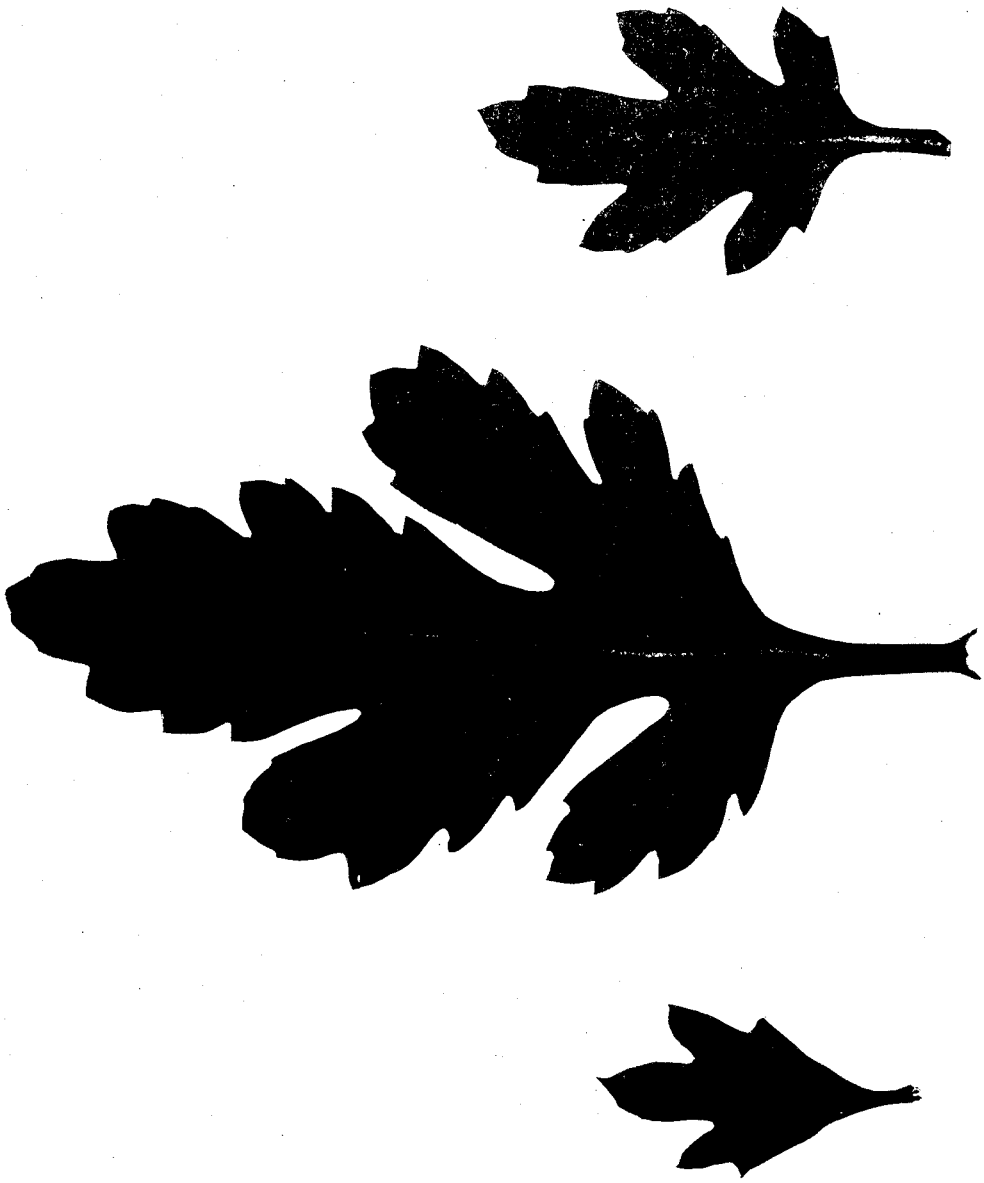

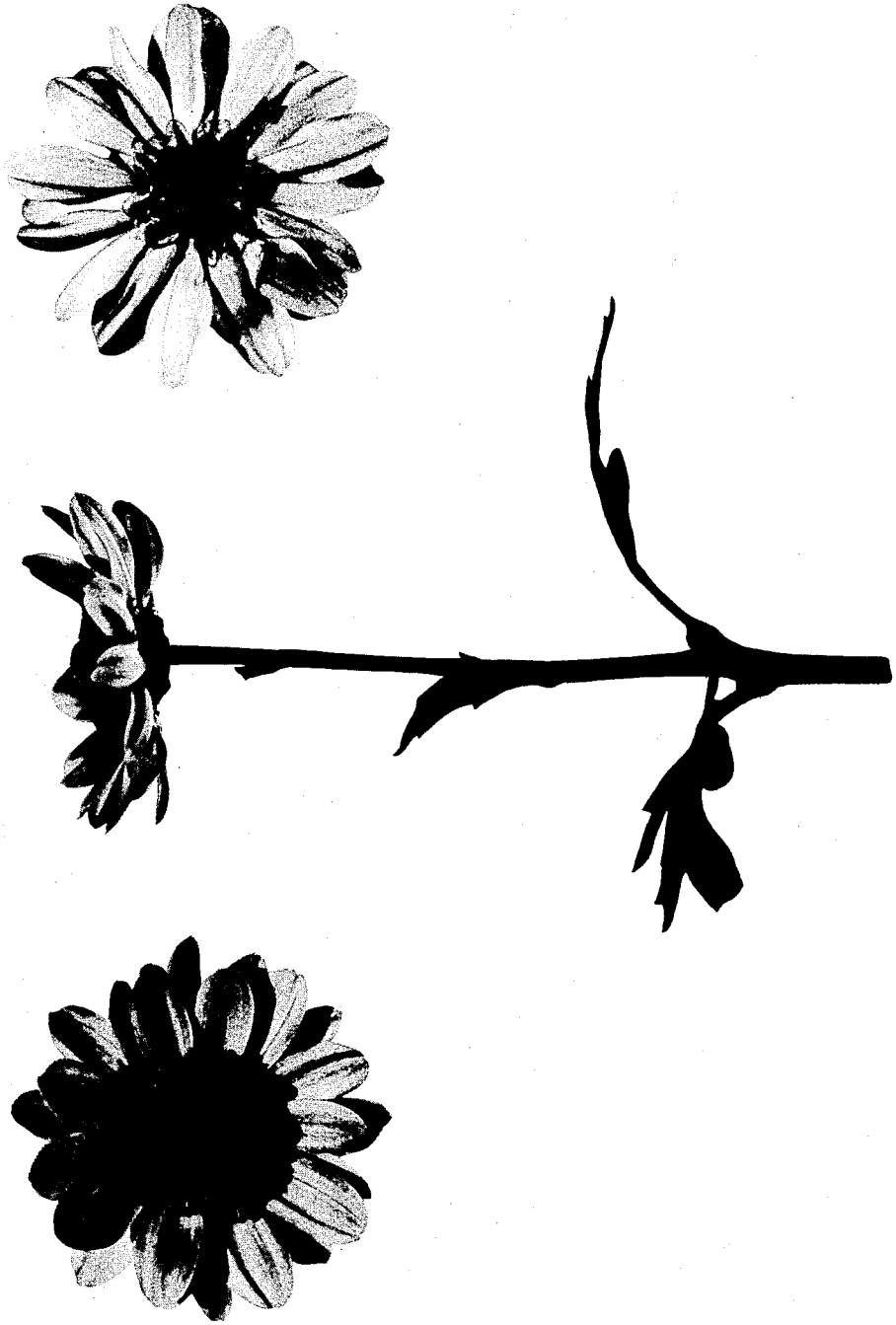

* * * * *